United States Patent
Pavlov et al.

(10) Patent No.: US 10,925,652 B2
(45) Date of Patent: Feb. 23, 2021

(54) OSTEOTOMY IMPLANT

(71) Applicants: RIOS MEDICAL AG, Stans (CH); IGNITE-CONCEPTS GMBH, Langendorf (CH)

(72) Inventors: Paul Pavlov, Nijmwegen (NL); Tom Overes, Langendorf (CH)

(73) Assignee: RIOS MEDICAL AG, Langendorf (CH)

( * ) Notice: Subject to any disclaimer, the term of this patent is extended or adjusted under 35 U.S.C. 154(b) by 147 days.

(21) Appl. No.: 15/032,043

(22) PCT Filed: Sep. 4, 2014

(86) PCT No.: PCT/CH2014/000127
§ 371 (c)(1),
(2) Date: Apr. 25, 2016

(87) PCT Pub. No.: WO2015/061917
PCT Pub. Date: May 7, 2015

(65) Prior Publication Data
US 2016/0287298 A1   Oct. 6, 2016

(30) Foreign Application Priority Data
Nov. 3, 2013 (CH) .................................. 1845/13

(51) Int. Cl.
*A61B 17/80* (2006.01)
*A61B 17/15* (2006.01)
(Continued)

(52) U.S. Cl.
CPC ........ *A61B 17/8095* (2013.01); *A61B 17/151* (2013.01); *A61B 17/154* (2013.01);
(Continued)

(58) Field of Classification Search
CPC ............ A61B 17/8095; A61B 17/8004; A61B 17/8028; A61B 17/8057; A61B 17/808;
(Continued)

(56) References Cited

U.S. PATENT DOCUMENTS 6,565,570 B2 *  5/2003  Sterett .................. A61B 17/025
606/280
8,137,406 B2     3/2012  Novak et al.
(Continued)

FOREIGN PATENT DOCUMENTS

CN    102247206 A    11/2011
WO    2008039508 A2    4/2008
(Continued)

OTHER PUBLICATIONS

Taiwan Intellectual Property Office, Office action from TPO dated Jun. 13, 2019, in application No. TW103136593.

*Primary Examiner* — Kevin T Truong
*Assistant Examiner* — Tracy L Kamikawa
(74) *Attorney, Agent, or Firm* — MU P.C.

(57) ABSTRACT

The present inventions relates to an osteotomy implant for bridging an osteotomy opening or resection in a target bone in a substantially countersunk manner. The osteotomy implant comprises a proximal portion with at least one aperture for receiving at least one bone fixation element and a distal portion with at least one aperture for receiving at least one bone fixation element. At least one middle strut portion connects said proximal portion with said distal portion. Said at least one middle strut portion has a width which is equal to or smaller than a thickness of said at least one middle strut portion.

12 Claims, 14 Drawing Sheets

(51) Int. Cl.
  *A61B 17/16*  (2006.01)
  *A61B 17/00*  (2006.01)
  *A61F 2/46*   (2006.01)

(52) U.S. Cl.
  CPC ........ *A61B 17/157* (2013.01); *A61B 17/1675* (2013.01); *A61B 2017/00707* (2013.01); *A61F 2002/4687* (2013.01)

(58) Field of Classification Search
  CPC ... A61B 17/809; A61B 17/151; A61B 17/154; A61B 17/157; A61B 17/1675; A61B 17/1728; A61B 17/1764; A61B 2017/00707; A61F 2002/4687
  USPC .............................................. 606/87–88, 293
  See application file for complete search history.

(56) References Cited

U.S. PATENT DOCUMENTS

| | | |
|---|---|---|
| 8,540,777 B2 | 9/2013 | Ammann et al. |
| 2004/0111089 A1 | 6/2004 | Stevens et al. |
| 2004/0172028 A1 | 9/2004 | Roger |
| 2005/0075641 A1 | 4/2005 | Singhatat et al. |
| 2005/0251147 A1* | 11/2005 | Novak ................... A61B 17/15 606/87 |
| 2007/0093834 A1 | 4/2007 | Stevens et al. |
| 2008/0140213 A1* | 6/2008 | Ammann ............... A61B 17/15 623/20.32 |
| 2008/0312742 A1* | 12/2008 | Abernathie ............. A61F 2/447 623/17.16 |
| 2010/0305704 A1 | 12/2010 | Messerli et al. |
| 2012/0323330 A1* | 12/2012 | Kueenzi .................. A61F 2/44 623/17.16 |
| 2013/0123923 A1 | 5/2013 | Pavlov et al. |
| 2015/0182236 A1* | 7/2015 | Dardenne ............. A61B 17/17 606/281 |

FOREIGN PATENT DOCUMENTS

| | | |
|---|---|---|
| WO | 2008048684 A2 | 4/2008 |
| WO | 2008066756 A2 | 6/2008 |
| WO | 2011155931 A1 | 12/2011 |

\* cited by examiner

OSTEOTOMY IMPLANT

TECHNICAL FIELD

The invention relates to surgical devices for performing opening wedge and closing wedge osteotomies of the knee.

BACKGROUND ART

Knee osteotomy is a surgical method used to realign the Mikulicz-line of the large joints of the lower limb, namely the hip, knee and ankle. With normal axial alignment of the limb the centre of the hip, the inter-condylar eminence of the tibial plateau and the centre of the ankle joint are in one line, the mechanical axis of the lower limb.

Due to for example arthritic damage on one side of the knee, born misalignment, or trauma injury, this alignment can be disturbed and cause excessive wear of the knee cartilage, known as knee-arthroses.

The purpose of the knee osteotomy surgical technique is to re-divide the forces in the knee in an early stage away from the damaged area to the opposite healthier side of the knee. Forces stemming from the patient's body weight and muscular reaction forces are better spread over the knee joint.

Two techniques are common in clinical practice, namely the opening wedge osteotomy and the closing wedge osteotomy. Both techniques aim to partly or fully re-establish the aforementioned Mikulicz-line.

When performing the closing wedge technique, a wedge of bone under the tibial plateau is removed. The tibial plateau is pulled down to close the gap and fixated with traumatology plates and screws.

When performing the opening wedge technique, a horizontal bone cut is made under the tibia plateau, over about 80% of the surface area. A wedge shaped spacer is inserted. The tibial plateau is forced up on one side, to correct the leg axis. The wedge shaped spacer can be made of natural bone, artificial bone or other biocompatible or osteointegrative materials.

To keep the spacer in place it is usually fixated with trauma plates and screws.

The knee osteotomy surgery technique offers important benefits to the patient, as it can postpone the moment a patient needs to get total knee-replacement up to 10 years.

Despite these advantages, complications are often associated with this technique, which often causes the patient discomfort during recovery. One of the more important causes of pain is the prominence of plates and screws laying on top of the bone, causing soft tissue irritation.

U.S. Pat. No. 8,137,406 B2 (Arthrex Inc.) discloses an apparatus for performing open wedge, high tibial osteotomies of the knee. The apparatus comprises an osteotomy plate including a body with a front side and a back side, a protrusion extending from the backside of the body for disposition in a wedge like opening of the bone as well as a plurality of mounting holes for receiving fixation screws. The mounting holes are formed such that when the protrusion is positioned in the wedge like opening, the fixation screws are directed into bone on either side of the wedge like opening.

One major drawback of the apparatus as disclosed in U.S. Pat. No. 8,137,406 B2 is that the osteotomy plate spans a large section of the wedge like opening of the bone, thereby preventing bone ingrowth over this large section. Further, the bone plate has a shape which follows the contour of a patient's bone at the edge of the wedge like opening, thereby giving rise to prominence of the bone plate over the rim of the opening in cases where the shape of the bone plate does not exactly match the outer contour of the opening.

SUMMARY OF THE INVENTION

It is the object of the invention to create an osteotomy implant pertaining to the technical field initially mentioned which only marginally disturbs the ingrowth of bone in an osteotomy opening and which reduces the occurrence of prominence of any implant part.

The solution of the invention is specified by the features of claim 1. According to the invention an osteotomy implant which bridges an opening in a target bone in a substantially countersunk manner comprises a proximal portion with at least one aperture for receiving at least one bone fixation element and a distal portion with at least one aperture for receiving at least one bone fixation element. Further, the osteotomy implant includes at least one middle strut portion connecting said proximal portion with said distal portion. The at least one middle strut portion has a width which is equal to or smaller than a thickness of said at least one middle strut portion.

Provision of at least one middle strut portion with the described width to thickness ratio has the advantage that a sufficient support over the osteotomy opening is provided by the at least one middle strut portion, while soft tissue irritation due to prominence of the at least one strut portion is reduced. This is mainly due to the fact that the at least one middle strut portion is countersunk into the target bone. Additionally, as the width of the at least one middle strut portion may be kept relatively small; bone ingrowth into the open wedge is only marginally perturbed. Further, only a small fraction of the edge of the osteotomy opening is occupied by the implant, hence allowing the larger part of the edge to be occupied e.g. by bone replacement material or to be left open. Bone replacement material will gradually be absorbed and replaced by natural bone. If the osteotomy opening is left open, natural bone will gradually grow into the opening and close the gap.

In the present application, the term "countersunk" means that a respective part of the osteotomy implant is placed completely into the target bone, its surface being flush with the surface of the target bone.

Further, the width of the at least one middle strut portion is defined by the dimension of the surface which is placed substantially parallel to the edge of the osteotomy opening in a direction which is substantially at a right angle with a length axis of the bone.

Correspondingly, the thickness of the at least one middle strut portion is the dimension of the at least one middle strut portion which is at a right angle to said width and which is intended to extend into the cancellous bone.

The opening to be bridged is preferably a wedge shaped opening. The apertures are preferably configured as screw holes which may comprise a threaded inner circumference. In alternative preferred embodiments, the apertures may be configured to house any type of bone fastener, e.g. a pin or blade or any other suitable type of bone fastener.

The osteotomy implant according to the present invention preferably comprises one middle strut portion. However, in further preferred embodiments, the osteotomy implant may comprise more than one middle strut portion, such as two middle strut portions, three middle strut portions or more middle strut portions.

The osteotomy implant is preferably made of a biocompatible material, such as stainless steel, titanium, a biocompatible polymer such as polyetheretherketone (PEEK) or a biocompatible metal alloy.

In the context of the present application, the terms "proximal" and "distal" are used to define the position of a specific part of the osteotomy implant in relation to the attachment point of the limb into which said osteotomy implant is to be implanted from the body. I.e.

an element which is "distal" is further away of the attachment point of the limb to the body than an element which is "proximal".

Preferably, the at least one middle strut portion has a height which is larger than said width of said at least one middle strut portion. The length of the at least one middle strut portion is understood as the distance of the at least one middle strut portion spanning from said distal portion to said proximal portion. Providing a larger height than width allows spanning larger openings while still not blocking a large extend of the edge of the opening by the osteotomy implant.

Preferably, a ratio between the width and the thickness of said at least one middle strut portion is at least 1:1, preferably larger than 1:2.5. Such ratios have exhibited a very strong support of the opening while only marginally blocking the edge of the opening by the implant.

The at least one middle strut portion preferably has a cross-section which is rectangular. This provides the at least one middle strut portion with a good resilience against bending forces exerted over the opening in the target bone.

Further preferably, the at least one middle strut portion has a cuboid shape, i.e. all surfaces of the at least one middle strut portion are arranged at a right angle to each other. A cuboid shape allows providing a highly stable middle strut portion, especially against compressive and bending forces while keeping the size to a minimum.

Preferably, the proximal portion and/or the distal portion comprise two or more cylindrical bodies linked one to another and which have substantially parallel central axes, wherein each of these cylindrical bodies comprises one aperture for receiving a bone fixation element.

Provision of a cylindrical body around said apertures for receiving a bone fixation element increases the stability of the osteotomy implant, as any forces exerted on said apertures by bone fixation elements may be reliably transferred to the at least one middle strut portion without any risk of fracture of the osteotomy implant.

Preferably, the two or more cylindrical bodies are tapered towards an end which is intended to be inserted within the bone. Provision of tapered cylindrical bodies facilitates the insertion of the osteotomy implant into a bone.

Preferably at least one aperture has an axis which is oriented at an acute angle relative to the central axis of the respective cylindrical body. This allows anchoring the inventive osteotomy implant in a larger support area in the bone.

Preferably, said proximal portion and said distal portion both comprise two cylindrical bodies, wherein each aperture in said proximal and said distal portion has an axis diverging from the central axis of its respective cylindrical body by acute angles pointing in an opposite direction to each other. The axes are thereby more preferably arranged in a plane which is at a right angle to a length axis of said at least one middle strut portion, i.e. the axes diverge from each other within said plane. This allows maximizing the support area within the bone, as two bone anchors inserted in said apertures will point away of each other.

Preferably, the axes of the two apertures of said proximal portion and/or the axes of the two apertures of said distal portion are at an angle of at least 2°, more preferably of at least 8°, most preferably at an angle of 11° to 30° relative to each other.

Thereby, the axes are preferably lying in a plane which is at a right angle to a length axis of said at least one middle strut portion. It was found that with said preferred angles, an optimal anchoring of the proximal portion and/or of the distal portion within a bone may be achieved.

Preferably, the angle between said axes is symmetrically arranged relative to a length axis of said at least one middle strut portion, i.e. each axis encloses half the angle between itself and the length axis of said at least one middle strut portion. For example, if the angle between the axes is 15°, each axis will be angled at 7.5° from said length axis. The symmetrical arrangement of the axes has the advantage that the osteotomy implant may be used for osteotomies in the left and the right tibia. If the axes were not arranged in a symmetrical fashion relative to the length axis of the at least one middle strut portion, different osteotomy implants for osteotomies in the left and the right tibia would have to be provided.

Alternatively, the angle between said axes is asymmetrically arranged relative to a length axis of said at least one middle strut portion. Hence, different osteotomy implants adapted for the left and the right tibial bone may be provided. An advantage of providing an osteotomy implant for the left and the right tibia is that an outer contour of the osteotomy implant, especially of the at least one middle strut portion may be specifically shaped to conform to the outer shape of the cortex of the tibia, hence reducing the prominence of the osteotomy implant and hence the risk of soft tissue irritation.

Generally, the smaller the angle between the axes is, the longer bone fixation elements may be used without risking any protuberance of the bone fixation elements out of the bone, e.g. on the side of the bone which is opposite the location of said osteotomy implant.

Further preferably, said axes may be arranged such that they are inclined towards the caudal or cranial direction once the osteotomy implant is implanted into a bone. In essence, the axes of the apertures of either said distal portion and/or said proximal portion are arranged in a plane which is arranged at an inclination angle relative to a plane spanned by the central axes of the respective cylindrical bodies. Said inclination angle preferably is from 1° to 15°, more preferably from 3° to 6°. Most preferably, the axes of the apertures of the proximal portion are arranged such as to be oriented in a cranial direction and the apertures of the distal portion such as to be oriented in a caudal direction once the osteotomy implant is implanted into a bone.

Alternatively, the axes of two apertures of said proximal portion are at an angle larger than 30°, preferably of 65° to 75° relative to each other.

Further preferably, the axes of two apertures of said distal portion are likewise at an angle larger than 30°, preferably of 65° to 75° relative to each other.

Preferably, said proximal portion and/or said distal portion comprises two cylindrical bodies linked one to another and each comprising an aperture with an axis, the axes of said apertures being parallel to each other.

In an alternatively preferred embodiment, said proximal portion and/or said distal portion comprises two cylindrical bodies linked one to another, and each comprising an aperture with an axis, wherein the axes of said apertures are arranged such as to intersect each other, preferably at a location within the target bone.

The osteotomy implant preferably comprises a wedge shaped bone graft or wedge shaped artificial bone which may be assembled with the at least one middle strut portion. This allows to optimally bridge an osteotomy gap in a bone, as the bone graft or artificial bone provides for bone ingrowth such as to bridge the osteotomy gap while the osteotomy implant transmits any loads exerted on said osteotomy gap. The assembly of the wedge shaped bone graft or wedge shaped artificial bone preferably is of the form-fit type.

The present application is further directed at a kit comprising an osteotomy implant according to the present invention, at least one wedge shaped trial spacer element and a bone-bed preparation guide.

The wedge shaped trial spacer is used to transitionally fill and keep open a wedge shaped osteotomy gap while the bone-preparation guide is used. The bone-preparation guide comprises drilling and sawing guides such as to allow a surgeon to make the necessary bores and resection cuts to insert the osteotomy implant according to the present invention.

Other advantageous embodiments and combinations of features come out from the detailed description below and the totality of the claims.

BRIEF DESCRIPTION OF THE DRAWINGS

The drawings used to explain the embodiments show:

FIGS. 5a-5i preferred surgical steps using a trial spacer instrument and a bone-bed preparation instrument to implant an osteotomy implant according to the present invention;

In the figures, the same components are given the same reference symbols.

PREFERRED EMBODIMENTS

Figure 1A:
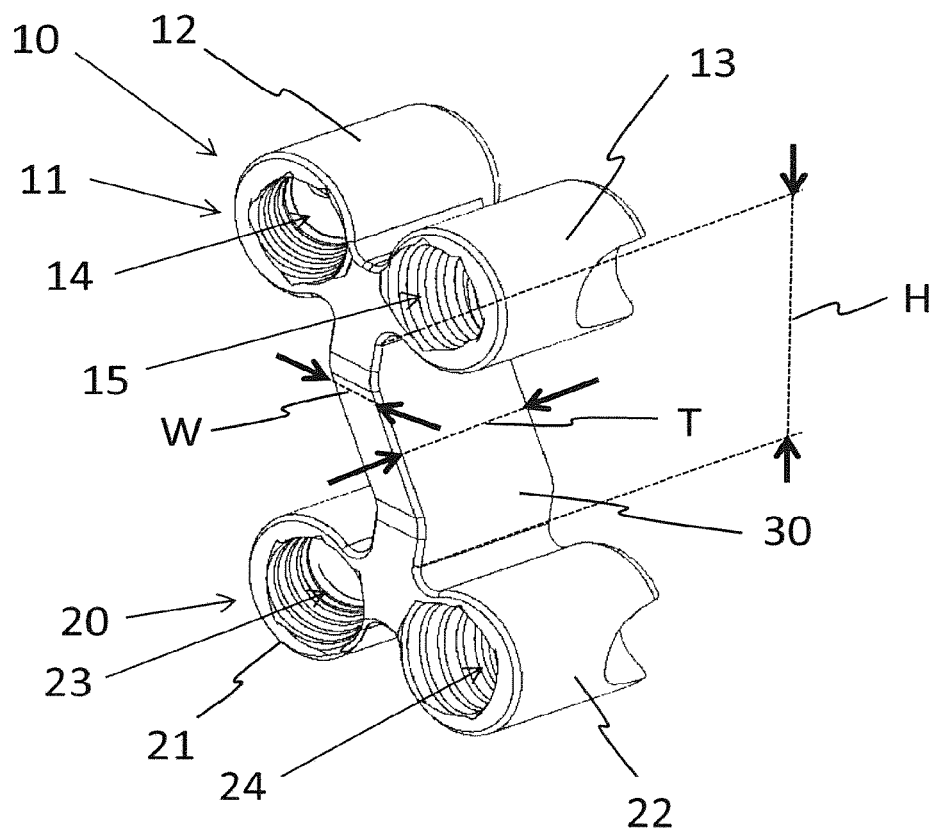
FIG. 1a, 1b an osteotomy implant assembly with an osteotomy implant according to the present invention.
Figure 1B:
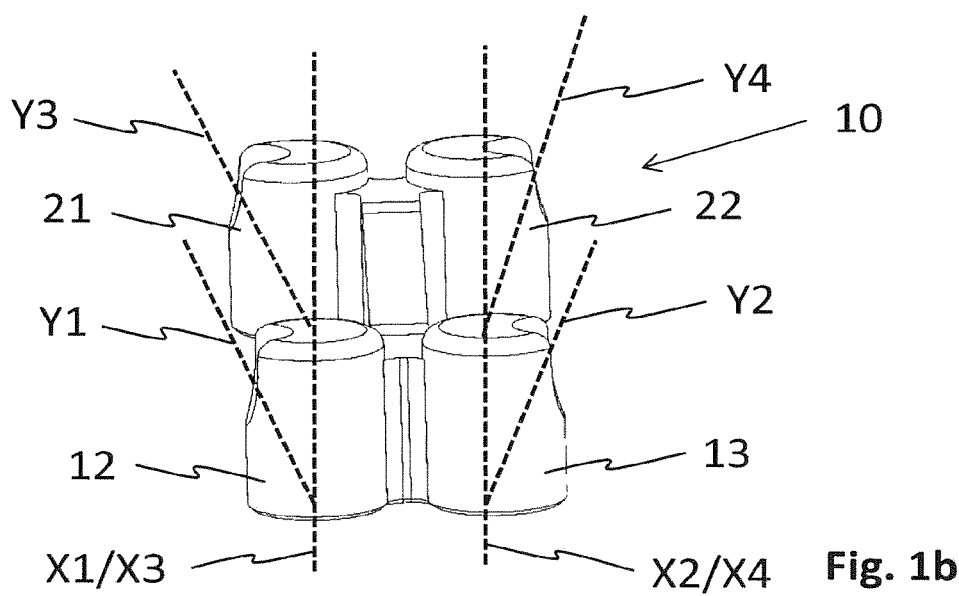

FIGS. 1a and 1b show an osteotomy implant assembly 1 for bridging an osteotomy opening or resection in a target bone in a substantially countersunk manner. The osteotomy implant 10 comprises a proximal portion 11 with two coinciding or linked cylindrical bodies 12, 13 with substantially parallel central axes X1, X2. The first cylindrical body 12 and the second cylindrical body 13 each comprise an aperture 14, 15 for receiving a bone-fixation element. In a preferred embodiment, the apertures 14, 15 are obliquely oriented, resulting in a diverging orientation of their respective axes Y1, Y2.

Furthermore the implant 10 comprises a distal portion 20 with two coinciding or linked cylindrical bodies 21, 22 with substantially parallel central axes X3, X4. The third cylindrical body 21 and the fourth cylindrical body 22 also each comprise an aperture 23, 24 for receiving a bone-fixation element. In a preferred embodiment, the two apertures 23, 24 of the distal portion 20 are obliquely oriented, resulting in a diverging orientation of their respective axes Y3, Y4.

The proximal portion 11 and the distal portion 20 are connected by a middle strut portion 30 of quadrangular cross-section, wherein the width W of the middle strut portion 30 is equal or smaller than the depth or thickness T of the middle strut portion 30. In a preferred embodiment, the connecting middle strut portion 30 has a width W to thickness T ratio of at least 1:1, preferably of larger than 1:2.5.

On the contrary to state of the art bone plates, the thickness T is not kept small to prevent from soft tissue irritation, but due to the intended countersunk placement, the thickness T of the middle strut portion 30 has no relevance for soft tissue irritation. The front 31 of the connecting middle strut portion 30 is shaped anatomically to follow the outer contour of a target bone. In an alternative embodiment the proximal portion 11 and the distal portion 20 are connected by multiple middle strut portions (not shown).

In an alternative embodiment, the implant 10 may comprise an unequal amount of proximal cylindrical bodies 12, 13 and distal cylindrical bodies 21, 22 with apertures 14, 15, 23, 24 for receiving bone screws 50a-50d. For example the proximal portion 11 may comprise three cylindrical bodies, due to the larger cross-section of the bone toward its proximal end, and the distal portion 20 only two cylindrical bodies.

FIG. 1b illustrates the orientation of the axes Y1, Y2, Y3, Y4 of the four apertures 14, 15, 23, 24 within the osteotomy implant 10, which is shown from the proximal portion 11 towards the distal portion 20. The first cylindrical body 12 and the second cylindrical body 13 each have a central axis X1, X2 which are substantially parallel to each other. The same applies to the third cylindrical body 21 and fourth cylindrical body 22, which each have a central axis X3, X4, respectively. The two axes X3, X4 are also substantially parallel to the central axes X1, X2 of said first cylindrical body 12 and said second cylindrical body 13.

Further, the first aperture 14 has an axis Y1 which is arranged at an angle to the central axis X1 of the first cylindrical body 12. The same applies to the other three apertures 15, 23, 24, which each have an axis Y2, Y3, Y3 which is arranged at an angle to the central axis X2, X3, X4 of its respective cylindrical body 13, 21, 22. The axis Y2 of the second aperture 15 is to diverge into the opposite direction of the axis Y1 of the first aperture 14. The same applies to the axes Y3, Y4 of the third aperture 23 and the fourth aperture 24.

Figure 2A:
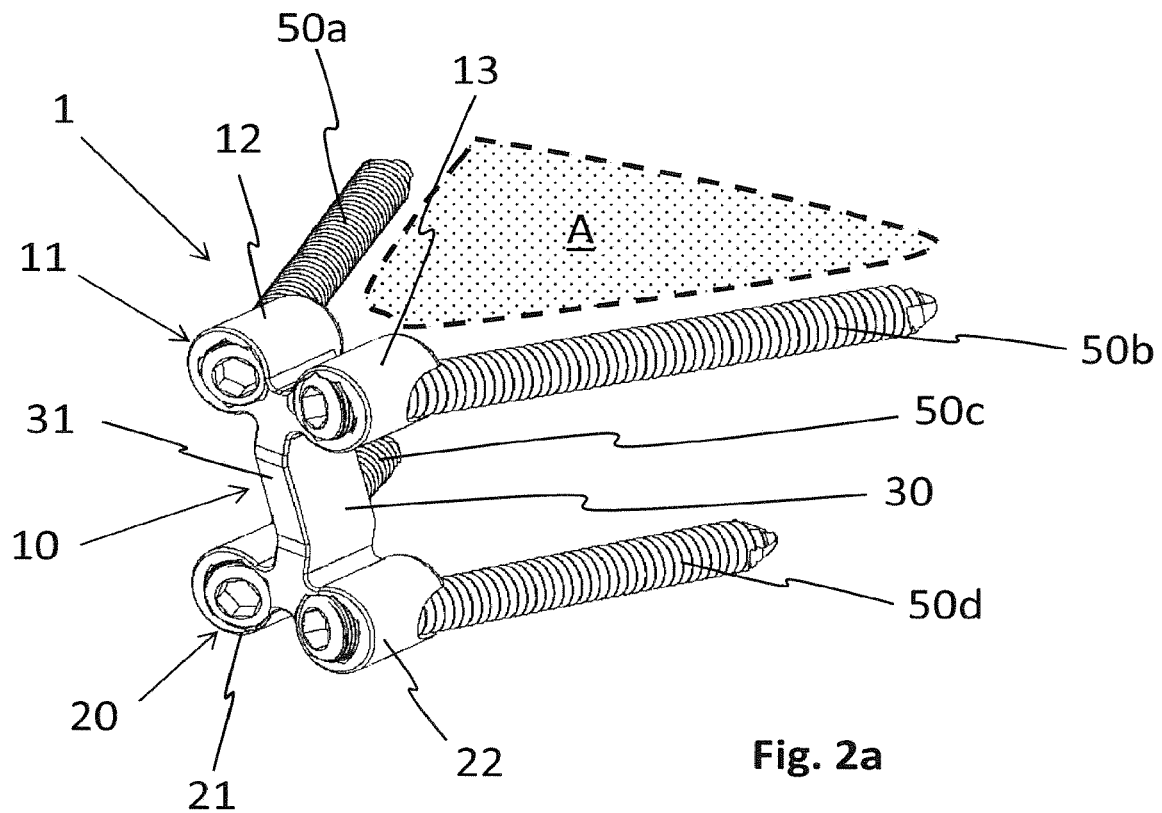
FIG. 2a, 2b the osteotomy assembly according to FIG. 1 with four bone screws.
Figure 2B:
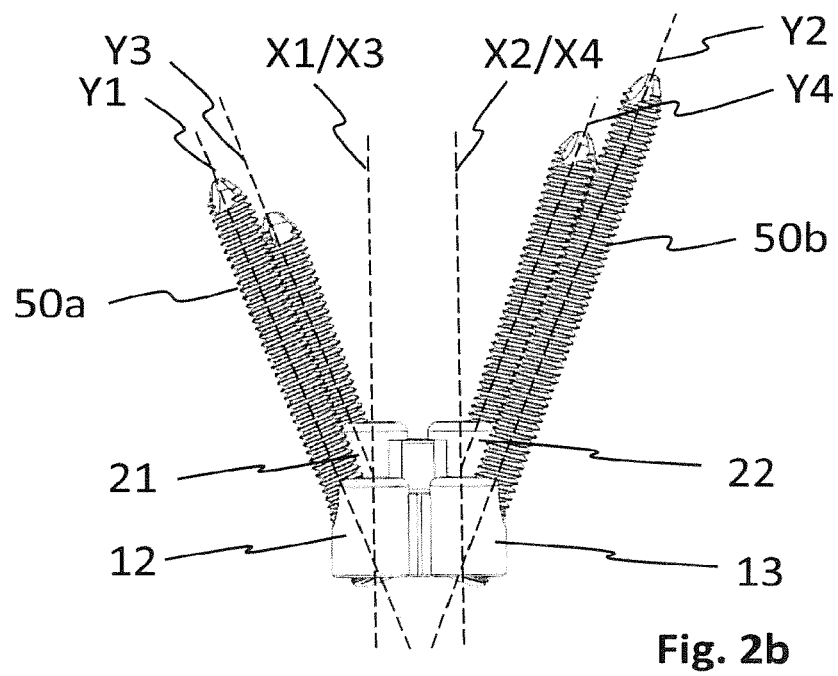

FIGS. 2a and 2b show an implant assembly 1 with an osteotomy implant 10 according to FIG. 1a as well as four bone screws 50a-50d. One bone screw is inserted into each of the four apertures 14, 15, 23, 24 of the osteotomy implant 10. The diverging axes Y1, Y2 of said first aperture 14 and said second aperture 15 lead to a divergence of the respective bone screws 50a, 50b. In consequence of the diverging bone screws 50a, 50b, a wider support area A in comparison to parallel placed bone screws 50a, 50b is obtained, wherein the implant 10 remains having a small overall width.

FIG. 2b shows the implant assembly 1 in the same perspective as FIG. 1b, however with the four bone screws 50a-50d inserted into said apertures 14, 15, 23, 24.

FIGS. 3a-3g show the different implantation steps for an open wedge osteotomy using an inventive osteotomy implant 10 according to the present invention.

Figure 3A:
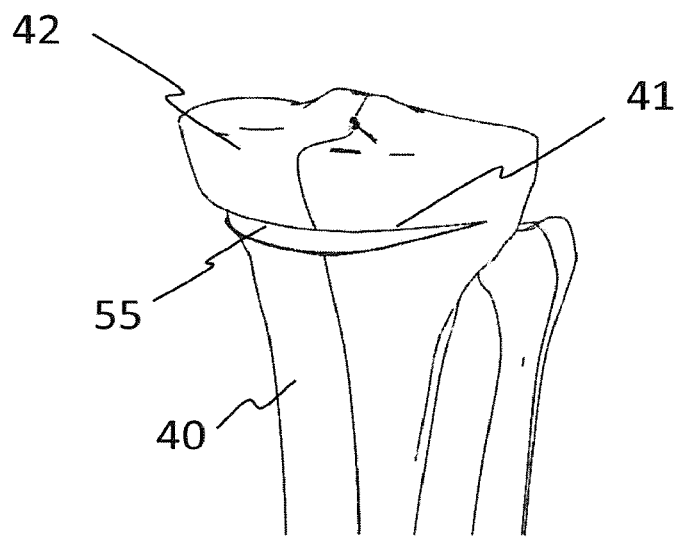
FIGS. 3a-3g different implantation steps for an open wedge osteotomy using an osteotomy implant according to the present invention.

FIG. 3a shows a wedge shaped bone graft 55 or alternatively an artificial implant inserted in an osteotomy opening 41 in a tibia bone 40. The wedge shaped bone graft 55 elevates the proximal portion 42 of the tibia and corrects the leg axis.

Figure 3B:
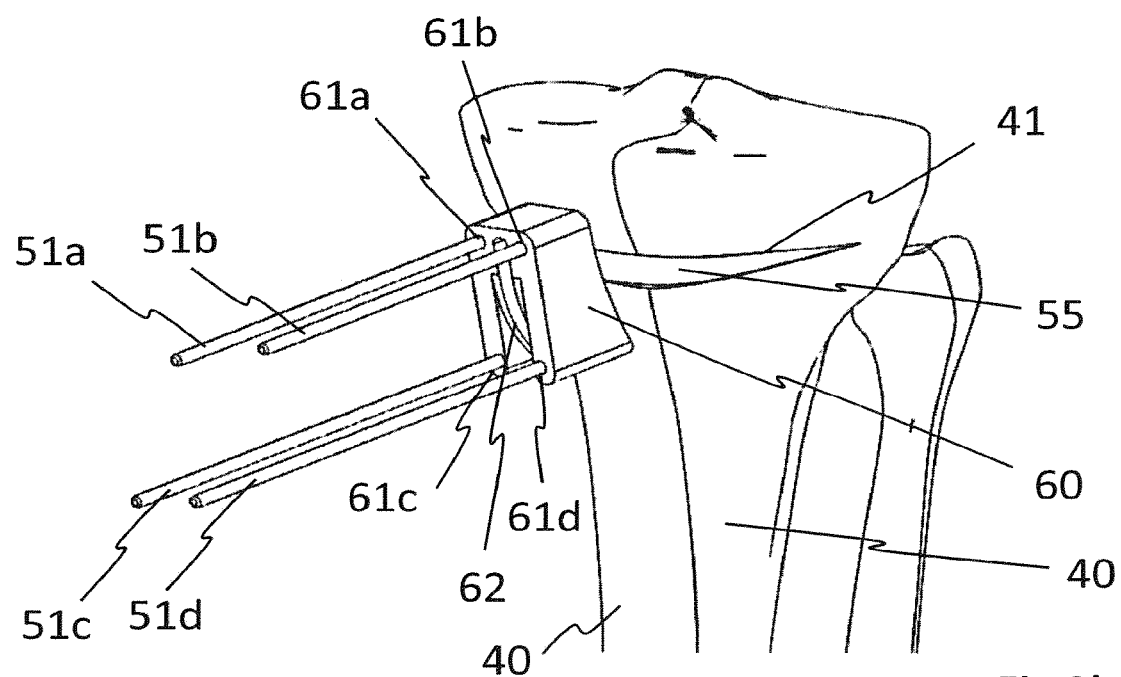

FIG. 3b shows a bone-bed preparation instrument 60 positioned against the tibia bone 40 and fixated with K-wires 51a-51d. The bone-bed preparation instrument 60 comprises multiple substantially parallel bores 61a-61d for receiving the K-wires 51a-51d as well as a saw or milling slot 62. The bone-bed preparation instrument 60 is positioned such as to bridge the osteotomy opening 41, wherein a first parallel bore 61a and a second parallel bore 61b are arranged on the proximal side of the osteotomy opening 41, while a third parallel bore 61c and a fourth parallel bore 61d are arranged on the distal side of the osteotomy opening 41.

Figure 3C:
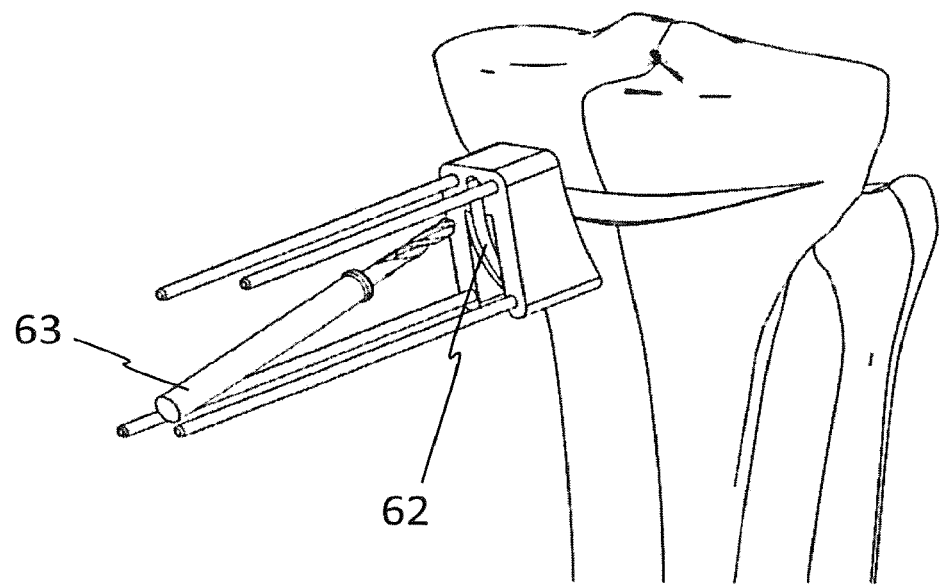
Figure 3D:
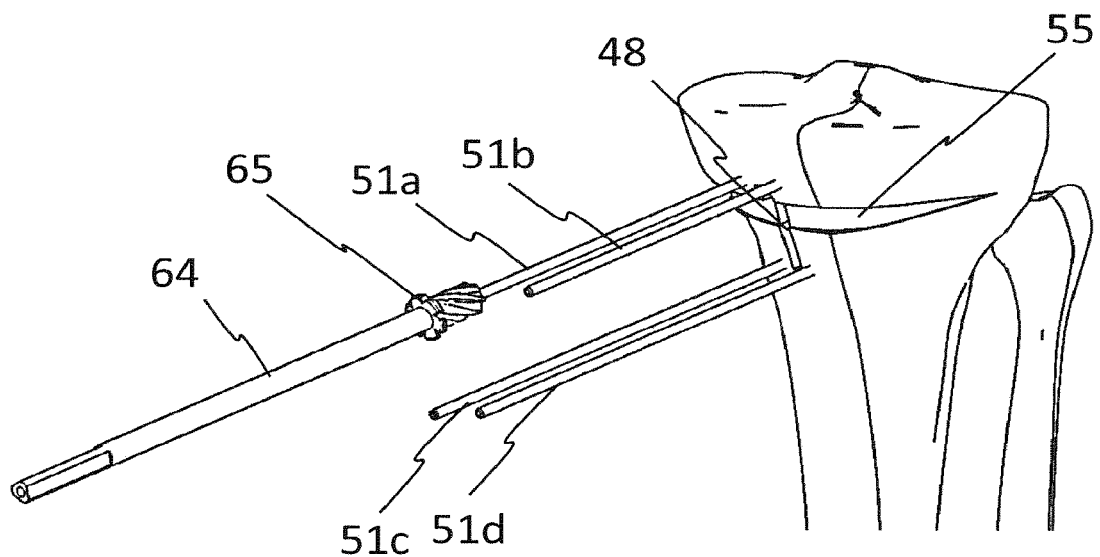

By sawing or milling through the milling slot 62 as shown in FIG. 3c, for example with a milling tool 63, a groove 48 is cut into the tibia bone 40 and the wedge shaped bone graft 55. Said groove 48 extends from the bone proximal of the osteotomy opening 41 to the bone distal of the osteotomy opening 41. In a following step the instrument is removed. Now, using a cannulated drill 64 with a stop 65, the K-wires 51a-51d are each over-drilled to a defined depth, as shown in FIG. 3d.

Figure 3E:
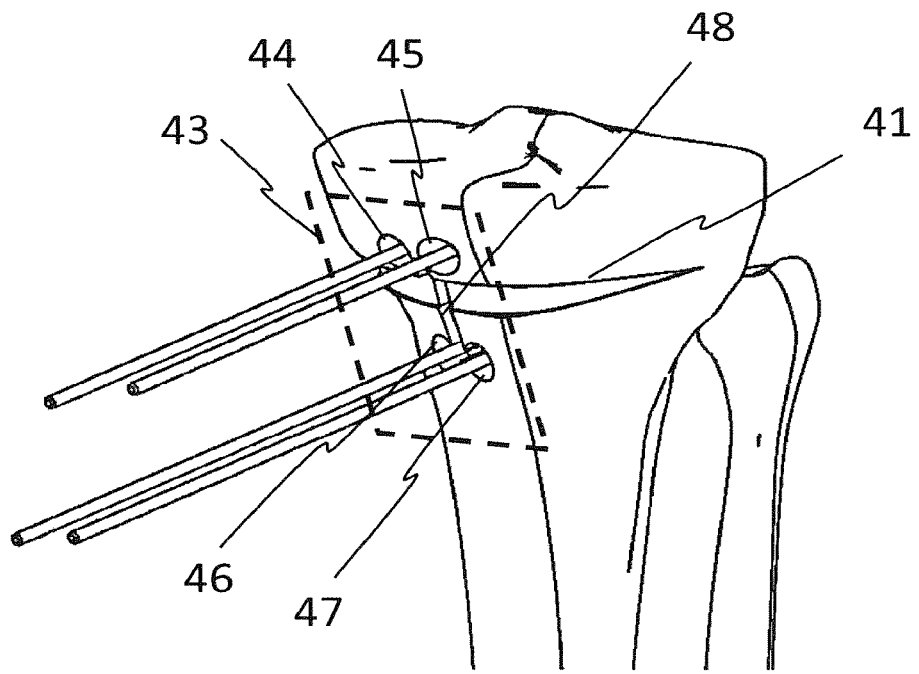

FIG. 3e shows the prepared bone bed 43 in the tibial bone 40 around the osteotomy opening 41. The bone bed 43 comprises a first bore 44 and a second bore 45 on the proximal side of the osteotomy opening 41, said two bores 44, 45 being linked together and being aligned substantially parallel to each other. Further, on the distal side of the osteotomy opening 41, a third bore 46 and a fourth bore 47 are located, said two bores being linked together and being arranged substantially parallel to each other. The groove 48 thereby spans from the proximal bores 44, 45 to the distal bores 46, 47.

Figure 3F:
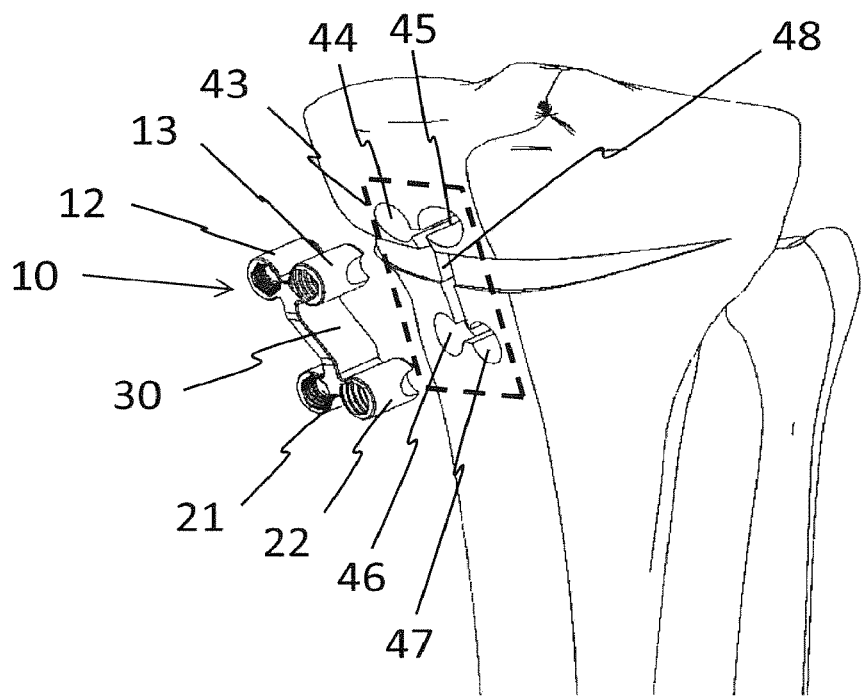

FIG. 3f shows the osteotomy implant 10 aligned with bone bed 43. The substantially parallel proximal cylindrical bodies 13, 14 and the distal cylindrical bodies 21, 22 of the osteotomy implant 10 align with the substantially parallel bores 44, 45, 46, 47 of the bone bed 43, while the middle strut portion 30 aligns with the groove 48.

Figure 3G:
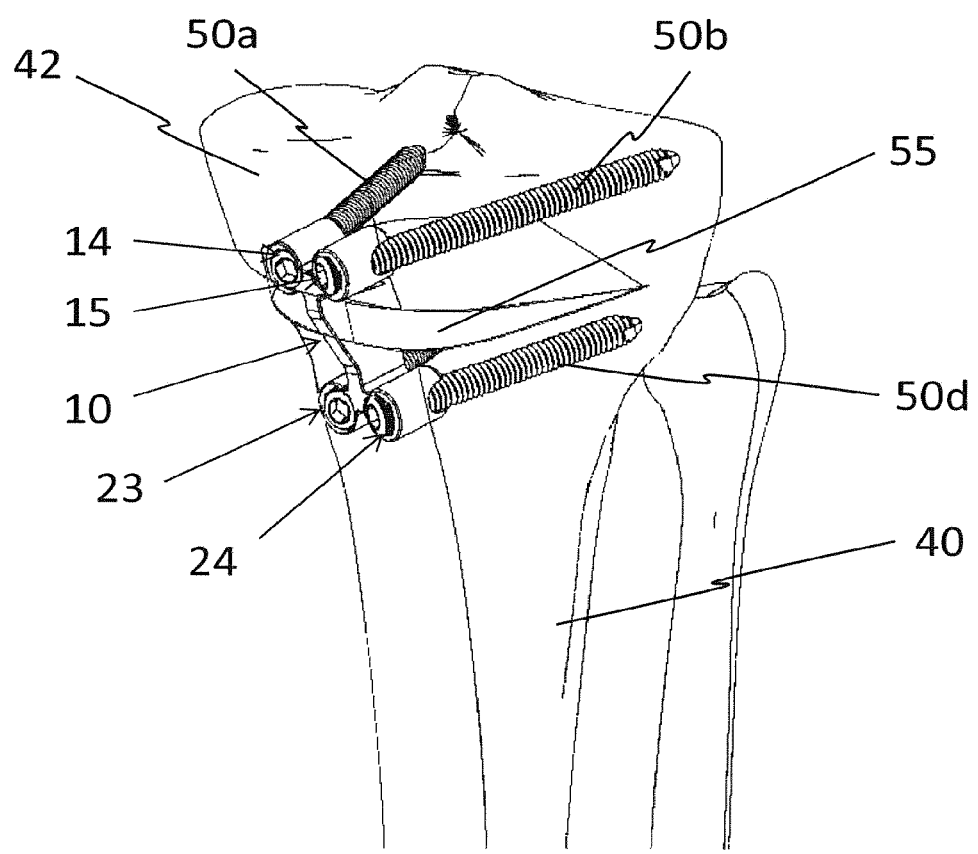

The implant 10 is then inserted in the bone bed 43 and bone screws 50a-50d are inserted into the four apertures 14, 15, 23, 24. FIG. 3g shows the implant assembly 1 implanted countersunk in tibia 40. The implant assembly 1 bridges the osteotomy opening 41, and transfers the bodyweight on the proximal tibia 42 to the distal tibia over the load-sharing construct of wedge 55 and osteotomy implant 10.

The implant assembly according to the above described technique is also suitable for stabilisation of a closed wedge osteotomy. In this case, insertion of a wedge shaped bone graft 55 into the osteotomy opening 41 is omitted.

In another alternative embodiment an insertion instrument (not shown) is attached to the osteotomy implant 10 to allow an insertion of the osteotomy implant 10 after preparation of the parallel bores 61a-61d and the milling slot 62. The insertion instrument comprises an extra set of openings, corresponding with the axes of the apertures 14, 15 in the proximal portion 11 and apertures 23, 24 in the distal portion 20. Through these openings, holes may be predrilled in the bone, which will receive the bone screws in a following step. Alternatively a drill-bushing with conical outer thread comprising an internal drill guiding channel may be locked into each aperture 14, 15, 23, 24. By drilling through theses bushings, holes may be drilled into the bone.

Figure 4A:
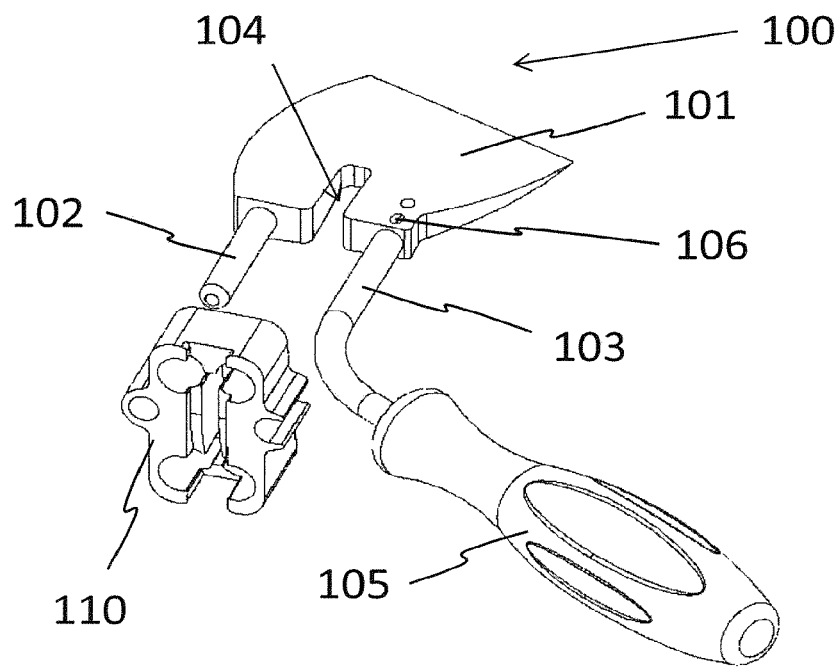
FIG. 4a, 4b instruments for a preferred surgical technique for implantation of an osteotomy implant according to the present invention.
Figure 4B:
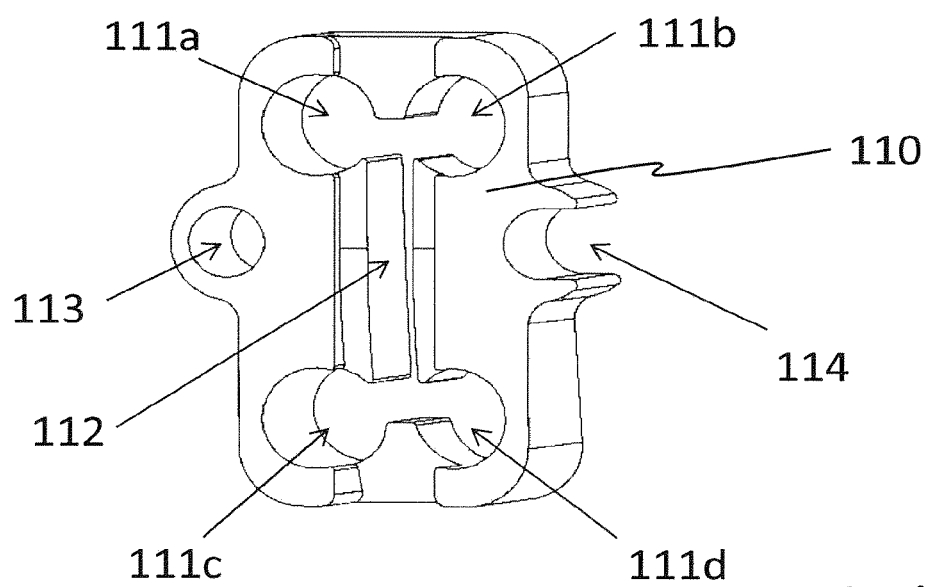

Referring to FIGS. 4a and 4b, instruments for a preferred surgical technique for implantation of the osteotomy implant 10 are shown. FIG. 4a shows a trial spacer instrument 100 comprising a wedge shaped body 101 with two cylindrical protrusions 102 and 103. Protrusion 103 ends in a bend shape and is connected to a handle 105.

Furthermore the wedge shaped body 101 comprises a recess 104 between the cylindrical protrusions 102 and 103. A fixation bore 106 is additionally arranged in said wedge shaped body 101.

Furthermore, a bone bed preparation instrument 110 is shown. Said bone bed preparation instrument is shown in more detail in FIG. 4b. The bone-bed preparation instrument 110 comprises multiple second parallel bores 111a-111d for guiding a drill with stop. Further, the bone-bed preparation instrument 110 includes a second saw or milling slot 112. The bone-bed preparation instrument 110 furthermore comprises a guiding bore 113 and a guiding recess 114 for assembly of the instrument onto trial spacer instrument 100.

FIGS. 5a to 5i show the preferred surgical steps using a trial spacer instrument 100 and a bone-bed preparation instrument 110 to implant the osteotomy implant 10.

Figure 5A:
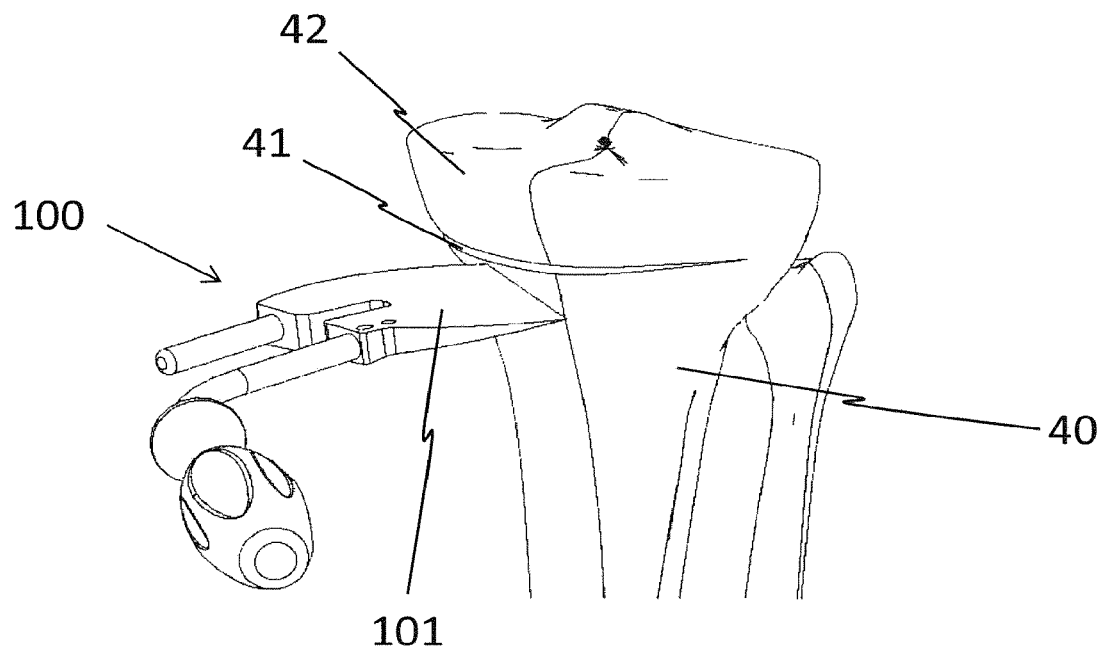
Figure 5B:
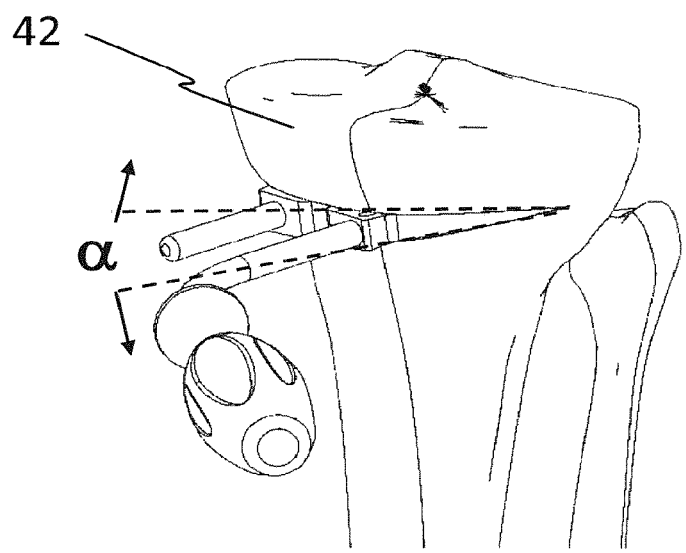

FIG. 5a shows the tibial bone 40 with partial osteotomy opening 41. The wedge shaped body 101 of the trial spacer instrument 100 is inserted in the osteotomy opening 41 which lift the proximal tibia 42. As shown in FIG. 5b, the proximal tibia 42 is lifted over an angle α. The angle α corresponds to the wedge angle of the wedge shaped body 101. Hence, a kit for osteotomy preferably comprises multiple trial spacer instruments 100 having wedge shaped bodies 101 with different angles such as to individually set the correction angle α.

Figure 5C:
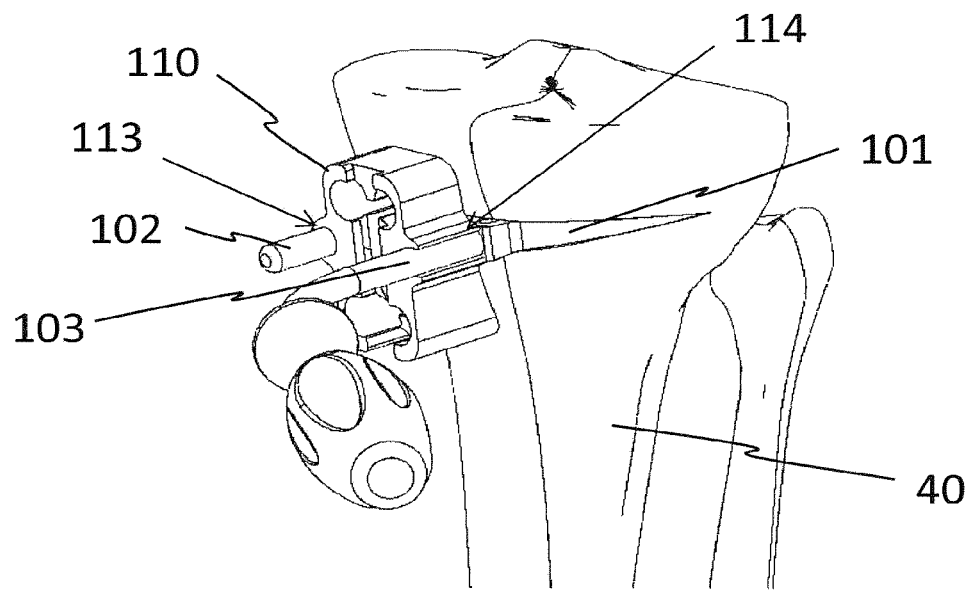

Next, as shown in FIG. 5c, the bone bed preparation instrument 110 is assembled onto the trial spacer instrument 100 such as to engage with the outer cortex of the tibial bone 40. Thereby, the bone bed preparation guide 110 is slideably assembled onto the trial spacer instrument 100, wherein guiding bore 113 and a guiding recess 114 are mating with the two cylindrical protrusions 102, 103 of the trial spacer instrument 110. The saw or milling slot 112 of the bone-bed preparation instrument 110 thereby aligns with the recess 104 of the wedge shaped body 101, wherein said recess 104 facilitates the passage of a milling or sawing tool as explained in greater detail later.

Figure 5D:
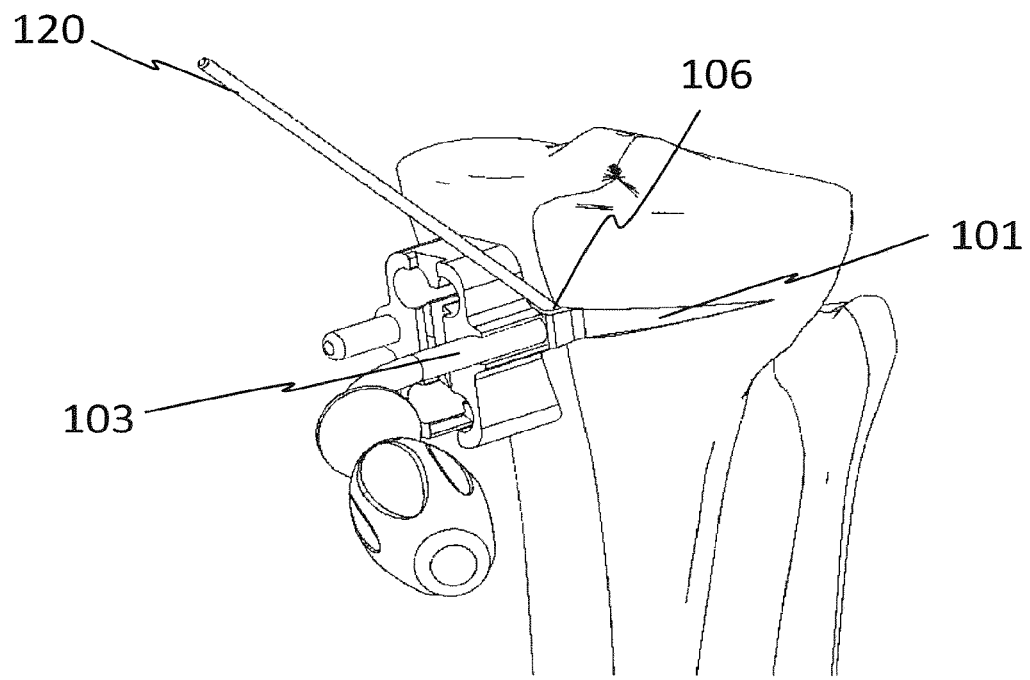

Optionally the assembly of trial spacer instrument 100 and bone bed preparation guide 110 is fixated to the bone using a K-wire 120 which is inserted into the fixation bore 106, as shown in FIG. 5d.

Figure 5E:
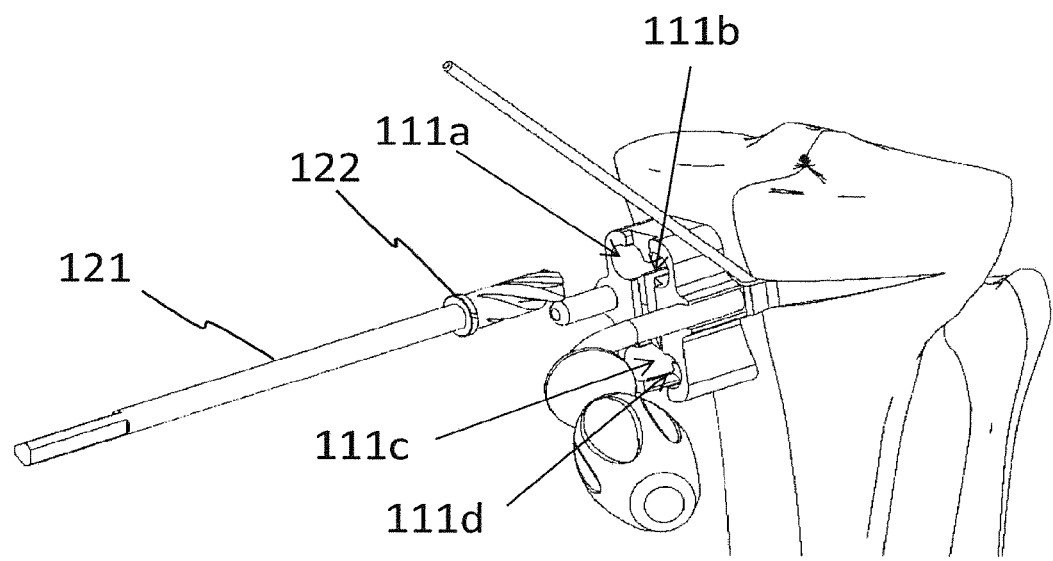

FIG. 5e shows a first bone bed preparation step. Using a drill 121 with a stop 122, four holes are drilled into the tibia 40 bone for receiving the osteotomy implant 10, wherein the drill is guided by the second parallel bores 111a-111d of the bone bed preparation instrument 110. Alternatively, the drill is not directly guided by the second parallel bores 111a-111d but by means of an intermediate element, such as a drill guide or drill bushing, placed into said second parallel bores 111a-111d. The advantage of using an intermediate element is that cutting edges of the drill may be fully surrounded by said intermediate element, thus avoiding that said cutting edges are caught and jammed against the area where the second parallel bores 111a-111d intersect the slot 112.

Figure 5F:
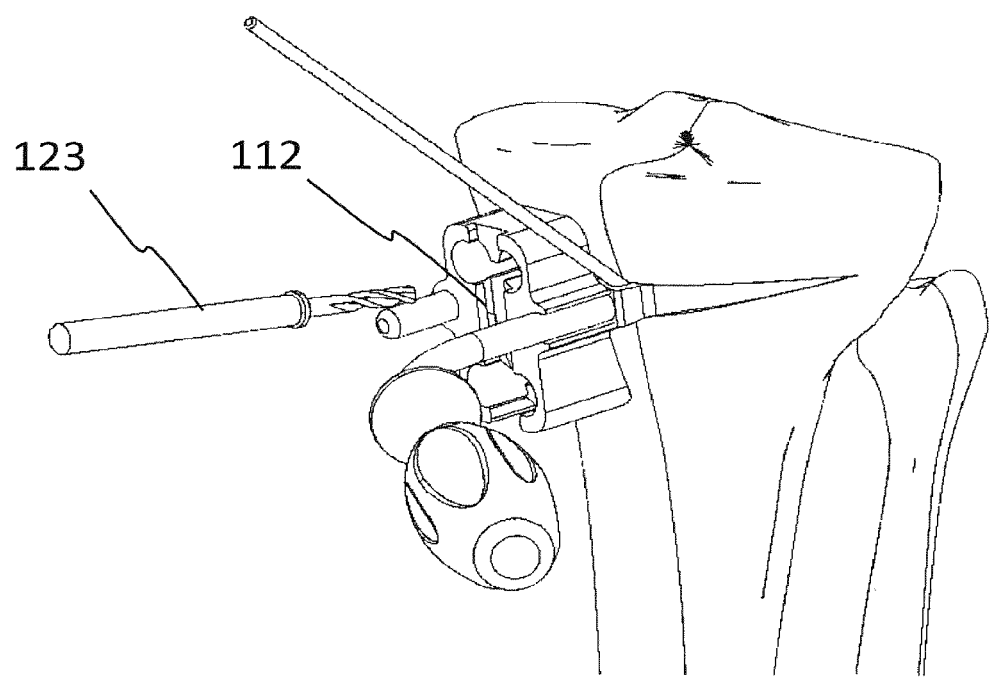

In a next step, as shown in FIG. 5f, by sawing or milling through the slot 112 a groove 48 is cut into the bone, extending from the bone proximal of the osteotomy opening 41 to the bone distal of the osteotomy opening 41. The sawing or milling is performed using a milling tool 123. Alternatively, the slot 112 may be substituted by two substantially parallel slots which guide an oscillating saw. Such slots may also be configured to converge towards each other.

Figure 5G:
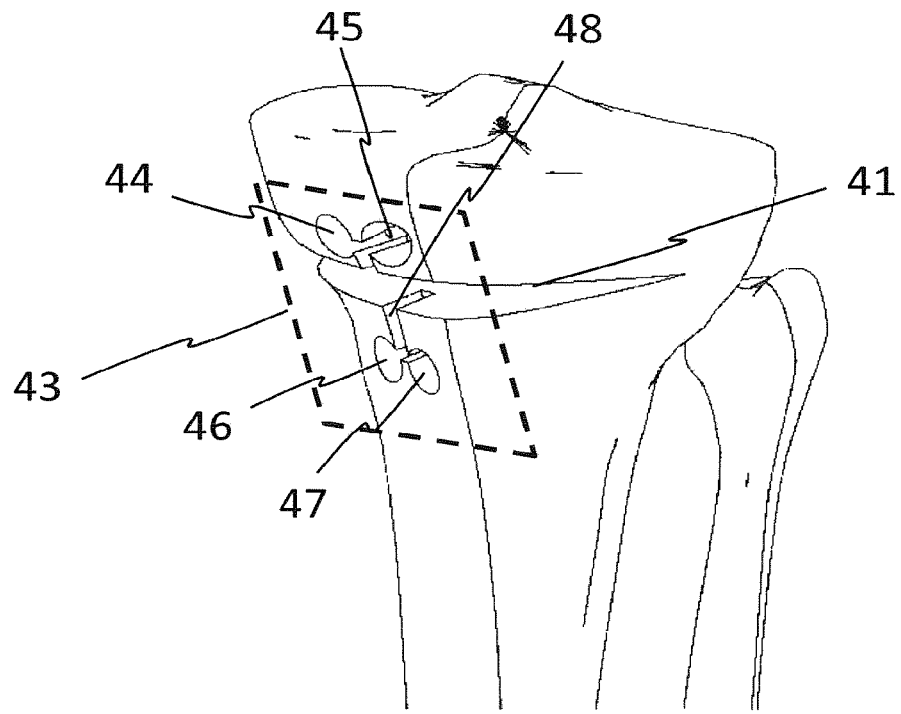

FIG. 5g shows the prepared bone bed 43 in the tibia bone 40 around the osteotomy opening 41 after removal of the instruments. The bone bed comprises two linked bores 44, 45 proximal of the osteotomy opening 41 as well as two linked bores 46, 47 distal of the osteotomy opening 41. Furthermore, the bone bed 43 includes one groove 48 which extends between the two bores 44, 45 proximal of the osteotomy opening 41 to the two bores 46, 47 distal of the osteotomy opening 41.

Figure 5H:
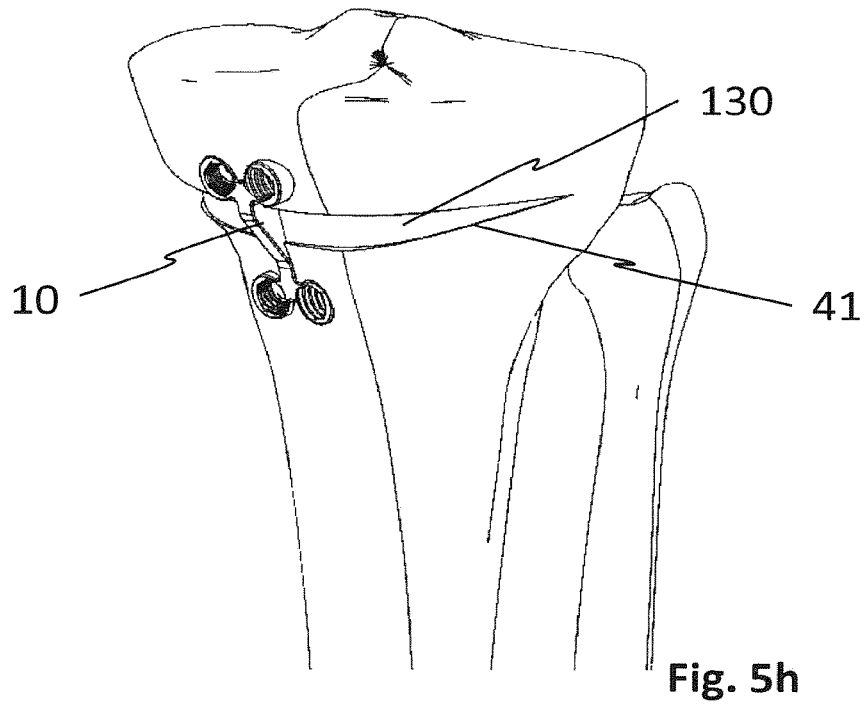

In a next step, as shown in FIG. 5h, the osteotomy implant 10 with attached bone graft wedge 130 is inserted into the osteotomy opening 41 and the bone bed 43. The bone graft wedge 130 is preferably made of a bone graft, but may also be made of plastic, for example Polyetheretherketone (PEEK), or a metal, for example porous titanium, or artificial bone substitutes or combinations thereof. Alternatively, no bone graft material is inserted into the osteotomy opening 41. Instead, the osteotomy opening 41 is left open such that natural bone may grow into and gradually seal the osteotomy opening 41.

Figure 6:
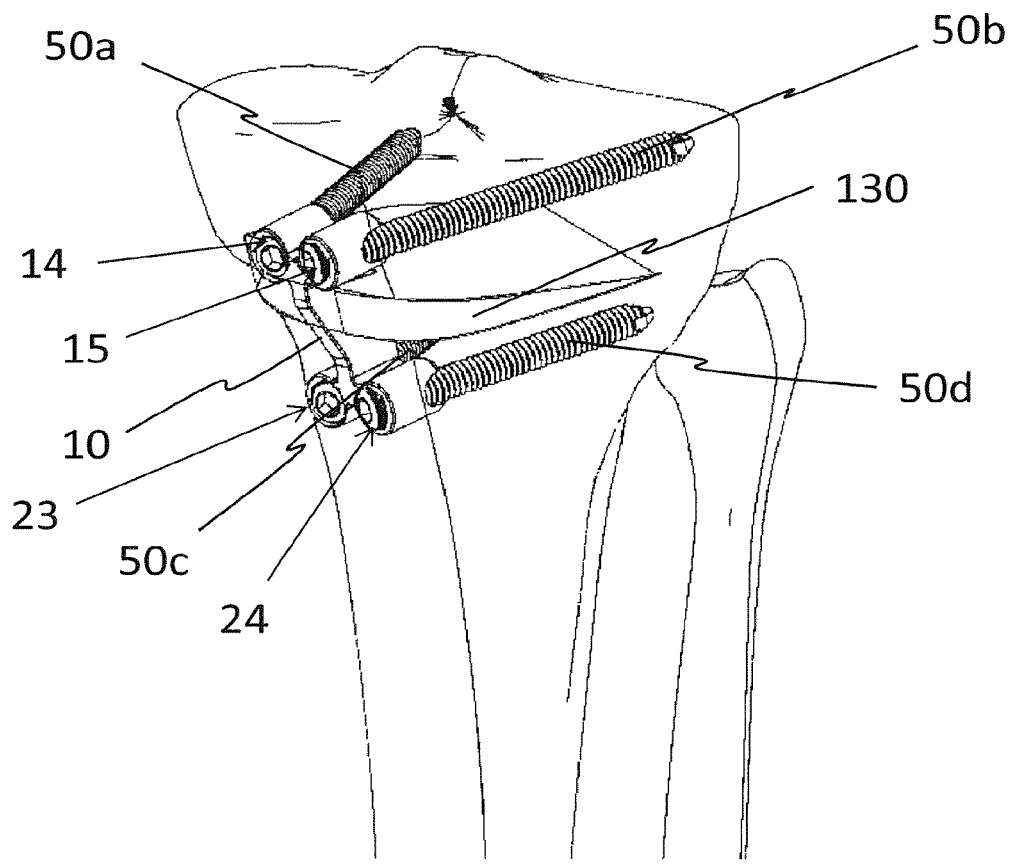
FIG. 6 multiple osteotomy implants according to the present invention with different lengths.
Figure 6:
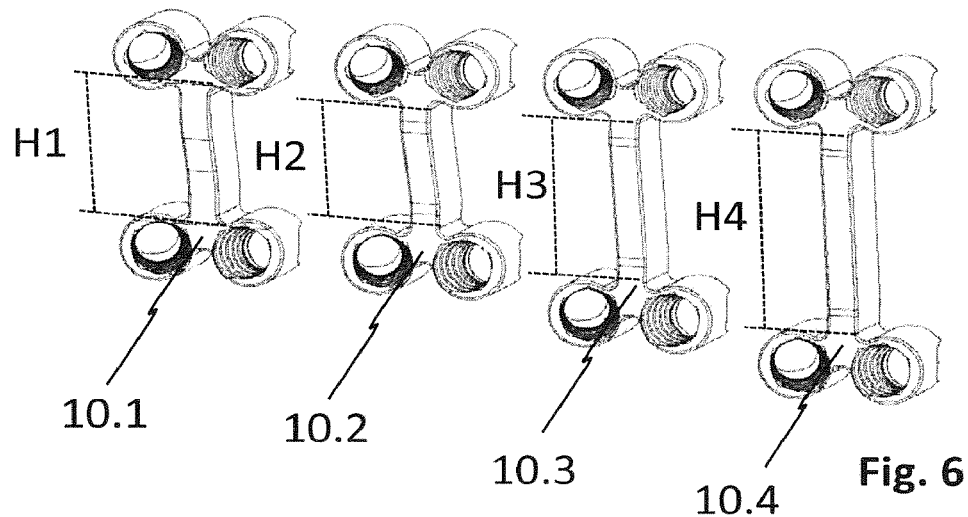

FIG. 5i shows the final fixation of the osteotomy implant 10 using bone screws 50a-50d. In an alternative embodiment the bone screws 50a-50d may be self-drilling bone screw and as a consequence no pre-drilling for placement of the bone screws 50a-50d would be necessary. In another alternative embodiment, a pin or a blade could be applied as a bone fixation element, or combinations thereof, wherein the apertures 14, 15, 23, 24 could be openings in a shape of a round hole, gap, slit or slot. FIG. 6 shows multiple osteotomy implants 10.1, 10.2, 10.3, 10.4 each having a different height H1, H2, H3, H4 of the middle strut portion 30 to match the patient's individual anatomy.

Figures 7A, 7B:
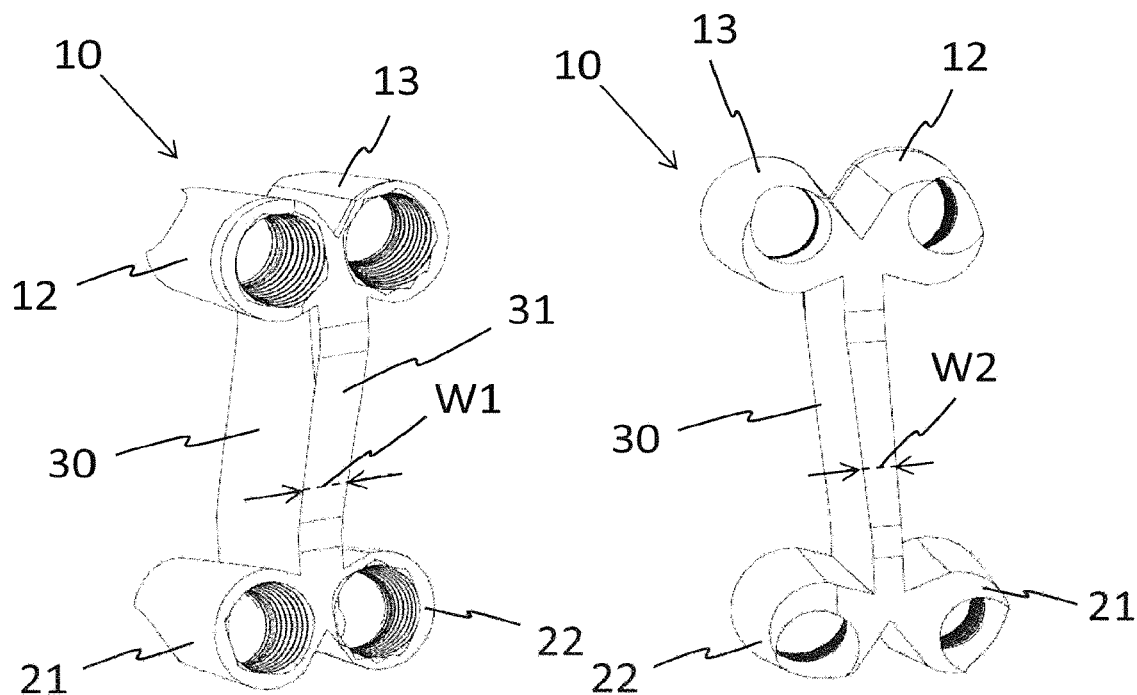
FIGS. 7a-7c a second embodiment of an osteotomy implant according to the present invention.
Figure 7C:
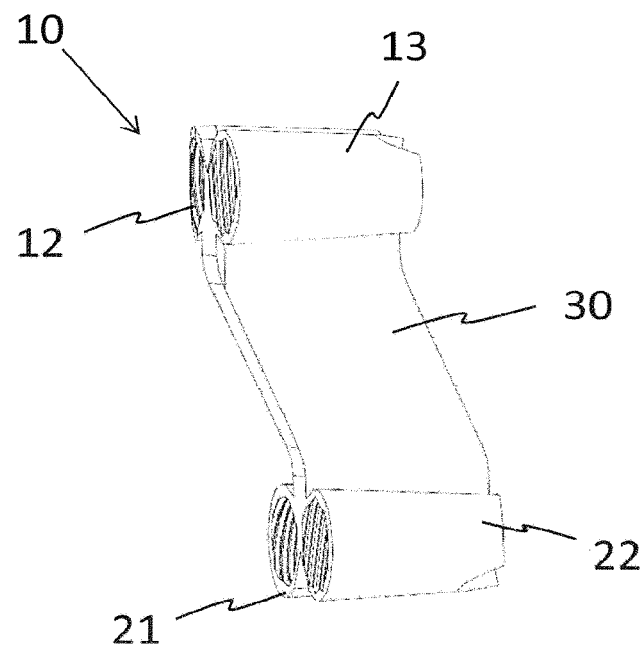

FIGS. 7a to 7c show a second embodiment of an osteotomy implant 10 according to the present invention. The middle strut portion 30 has different widths W1, W2 on its two sides. The side of the middle strut portion 30 which is intended to be arranged within the bone has a second width W2 which is smaller than the first width W1 on the front 31, which is intended to be arranged parallel to the cortex of the bone. This feature is recognizable by comparing FIG. 7a, which shows the osteotomy implant 10 from the front 31 and FIG. 7b which shows the osteotomy implant 10 from the side intended to be arranged within the bone.

Further, the four cylindrical bodies 12, 13, 21, 22 are tapered towards their end which is intended to be inserted within the bone, giving the four cylindrical bodies 12, 13, 21, 22 a slight conical shape, as may be seen by the side view of the osteotomy implant 10 as shown in FIG. 7c. Use of tapered cylindrical bodies 12, 13, 21, 22 facilitates the insertion of the osteotomy implant 10 into bone. As a person having skill in the art understands, the pre-drilled holes within the bone will preferably have an equally tapered shape.

Figure 8A:
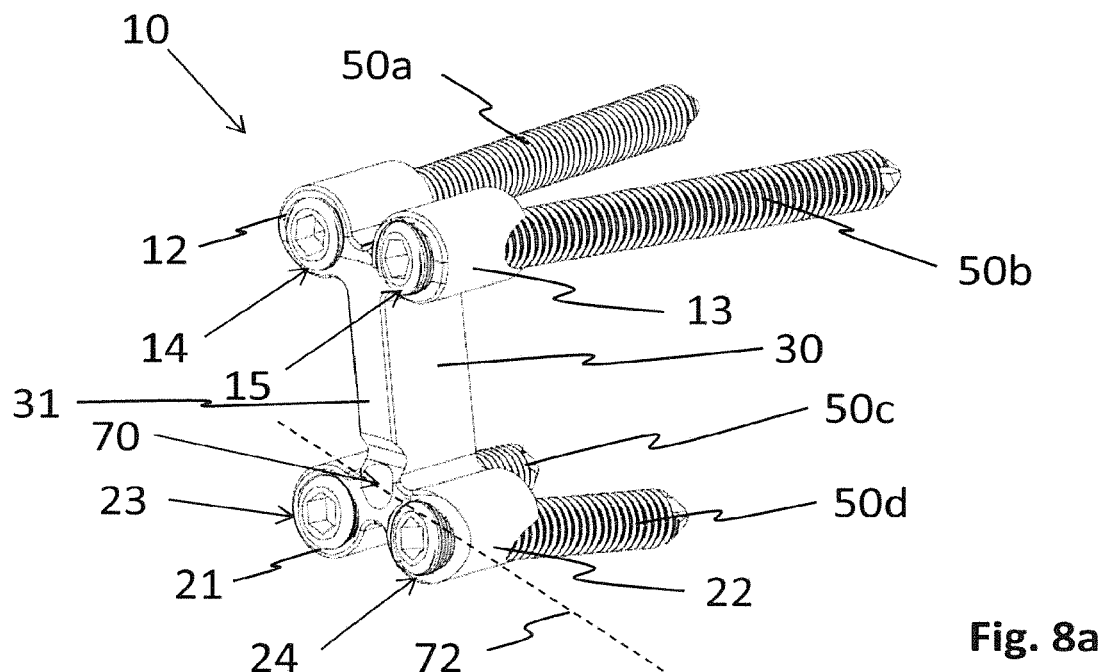
FIG. 8a, 8b a third embodiment of an osteo implant according to the present invention.
Figure 8B:
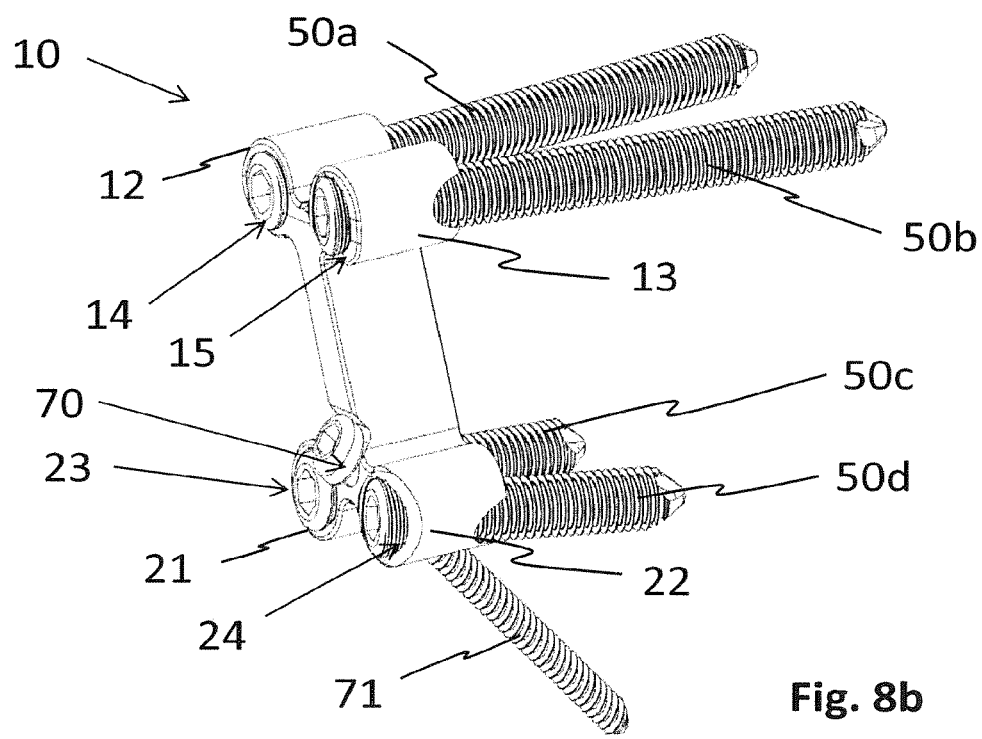

FIGS. 8a and 8b show a third embodiment of an osteotomy implant 10 according to the present invention. This embodiment corresponds largely to the embodiment as shown in FIG. 2. However, as shown in FIG. 8a, an additional fifth aperture 70 is arranged in the middle strut portion 30. The fifth aperture 70 has a central axis 72 which includes an acute angle to the front 31 of the middle strut portion 30. As seen in FIG. 8b, the fifth aperture 70 may receive a compression screw 71. The compression screw 71 helps establishing a compression force over the osteotomy opening 41, which helps the primary and secondary stability of the implant.

In another alternative embodiment, the instruments for implantation and the osteotomy implants are part of a single use kit. Different sizes of implants will require different bone preparation devices that correspond with the shape of the implant. An exemplary single use kit comprises combinations of the following components:
- an osteotomy implant 10;
- bone screws 50a-50d of different lengths;
- a pre-manufactured bone graft wedge 130;
- at least one trial spacer instrument 100;
- a bone-bed preparation instrument 110;
- a drill 121;
- a milling tool 123;
- a K-wire 51 for fixation of the bone-bed preparation instrument 100;
- a drill to pre-drill before insertion of the bone screws 50a-50d (not shown)
- an insertion instrument (not shown);
- a screwdriver (not shown).

The detailed description is focussed on opening wedge osteotomies, nevertheless, the osteotomy implant may also be used for closing wedge osteotomies. Furthermore, the osteotomy implant 10 as well as the various instruments could be adapted to be applied to other anatomical areas, for example to the distal femur, the proximal femur, the radius, the spine, etc.

We claim:

1. An osteotomy implant for bridging an osteotomy opening or resection in a target bone in a substantially countersunk manner, the osteotomy implant comprising:
   a) a proximal portion having at least one aperture for receiving at least one first bone fixation element;
   b) a distal portion having at least one aperture for receiving at least one second bone fixation element;
   c) at least one middle strut portion having a middle strut length axis defined along the greatest dimension of the middle strut portion, the middle strut length axis connecting the proximal portion with the distal portion such that the proximal portion and the distal portion are located at opposing ends of the middle strut portion along the middle strut length axis, and separated from each other by the greatest dimension of the middle strut portion,
   the at least one middle strut portion spanning lengthways from the proximal portion to the distal portion, the at least one middle strut portion having a width which is equal to or smaller than a thickness of the at least one middle strut portion, the width being defined by a dimension of the at least one middle strut portion which is at a right angle to the middle strut length axis, while the thickness being a dimension of the at least one middle strut portion which is at a right angle to the width and to the middle strut length axis, and which is intended to extend into the center region of the bone, wherein the proximal portion and/or the distal portion comprises two or more cylindrical bodies linked one to another, the two or more cylindrical bodies in the proximal portion being separated by a first separating portion, and having parallel central axes and/or the two or more cylindrical bodies in the distal portion being separated by a second separating portion, and having parallel central axes, wherein each of these cylindrical bodies comprises one aperture, of the at least one aperture of the proximal portion or the at least one aperture of the distal portion, such that the respective apertures of the two or more cylindrical bodies in the proximal portion are non-overlapping with respect to each other and with respect to any of the apertures of the distal portion, and the respective apertures of the two or more cylindrical bodies in the distal portion are non-overlapping with respect to each other and with respect to any one of the apertures of the proximal portion, for receiving the respective bone fixation element, and wherein the width of the at least one middle strut portion is smaller than a thickness of the two or more cylindrical bodies, the thickness of the two or more cylindrical bodies being measured along a line passing through the respective cylindrical body such that the line is parallel with a central axis of the respective cylindrical body.

2. The osteotomy implant according to claim 1, wherein the at least one middle strut portion has a length which is greater than the width of the at least one middle strut portion.

3. The osteotomy implant according to claim 1, wherein a ratio between the width and the thickness of the at least one middle strut portion is greater than 1:2.5.

4. The osteotomy implant according to claim 1, wherein the at least one middle strut portion has a cross-section which is rectangular.

5. The osteotomy implant according to claim 1, wherein the at least one middle strut portion has a cuboid shape.

6. The osteotomy implant according to claim 1, wherein the two or more cylindrical bodies each have a cylindrical middle portion and are tapered towards an end of each cylindrical body which is intended to be inserted within the bone.

7. The osteotomy implant according to claim 1, wherein at least one aperture of the at least one aperture of the proximal portion or the at least one aperture of the distal portion has an axis which is oriented at an acute angle relative to the central axis of the respective cylindrical body.

8. The osteotomy implant according to claim 7, wherein the axes of the two apertures of the proximal portion and/or the axes of the two apertures of the distal portion are at an angle of at least 2° relative to each other.

9. The osteotomy implant according to claim 7, wherein the axes of the two apertures of the proximal portion are at an angle greater than 30° relative to each other.

10. The osteotomy implant according to claim 7, wherein the axes of the two apertures of the distal portion are at an angle greater than 30° relative to each other.

11. The osteotomy implant according to claim 1, wherein the osteotomy implant further comprises a wedge-shaped bone graft or wedge-shaped artificial bone which may be assembled with the at least one middle strut portion.

12. A kit comprising an osteotomy implant according to claim 1, at least one wedge-shaped trial spacer element and a bone-bed preparation instrument.

* * * * *